United States Patent
De Baets

[19]

[11] Patent Number: 5,927,971
[45] Date of Patent: Jul. 27, 1999

[54] ORTHODONTIC DEVICE

[76] Inventor: Jan De Baets, Geneva, Switzerland

[21] Appl. No.: 08/578,554
[22] PCT Filed: Mar. 17, 1993
[86] PCT No.: PCT/EP93/00631
  § 371 Date: Jan. 3, 1996
  § 102(e) Date: Jan. 3, 1996
[87] PCT Pub. No.: WO93/18718
  PCT Pub. Date: Sep. 30, 1993

[30] Foreign Application Priority Data

Mar. 18, 1992 [CH] Switzerland .............................. 865/92

[51] Int. Cl.⁶ ...................................................... A61C 3/00
[52] U.S. Cl. ................................................ 433/17; 433/18
[58] Field of Search ................................ 433/16, 17, 18, 433/24, 8

[56] References Cited

U.S. PATENT DOCUMENTS

| | | | |
|---|---|---|---|
| 986,425 | 3/1911 | Montague | 433/16 |
| 1,481,861 | 1/1924 | Eaton | 433/17 X |
| 3,660,900 | 5/1972 | Andrews | 433/16 |
| 3,721,005 | 3/1973 | Cohen | 433/16 |
| 4,243,387 | 1/1981 | Prins | 433/16 |
| 4,496,317 | 1/1985 | Hulsey | 433/16 X |
| 5,302,121 | 4/1994 | Gagin | 433/16 X |

*Primary Examiner*—Nicholas D. Lucchesi

[57] ABSTRACT

A device for moving a tooth by combining translational motion with angular movement, comprising a holder attached to the tooth and provided with a device for attaching a pivotable element cooperating with a force exerting device. The pivotable element comprises plane sloping sides for engaging the holder and thereby limiting the angular movement of the tooth to a predetermined value. A cuneal member for adjusting the angle of slope may also be provided.

17 Claims, 2 Drawing Sheets

FIGURE 1
FIGURE 2A
FIGURE 2B
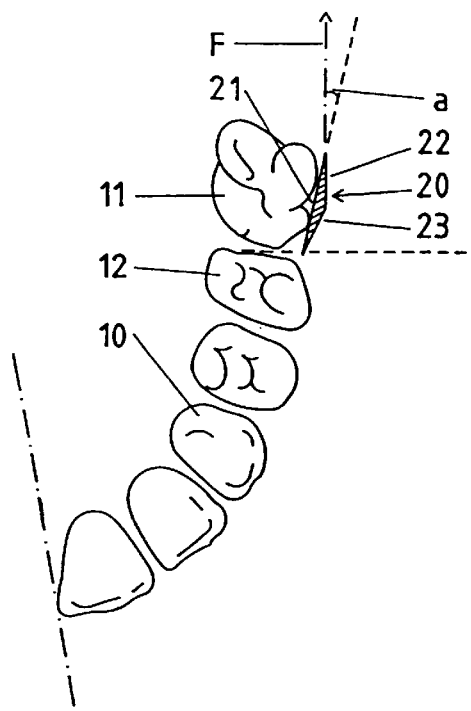
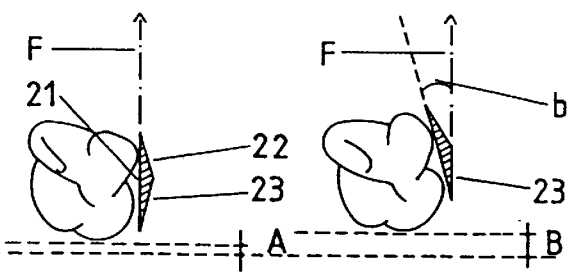
FIGURE 3
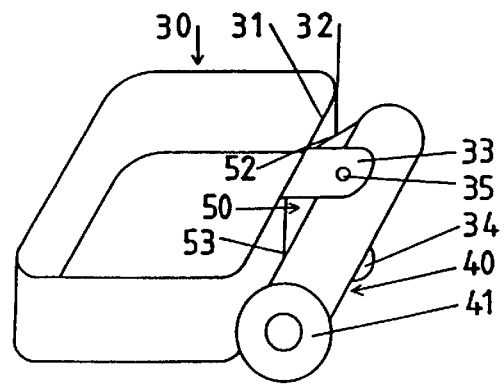
FIGURE 4
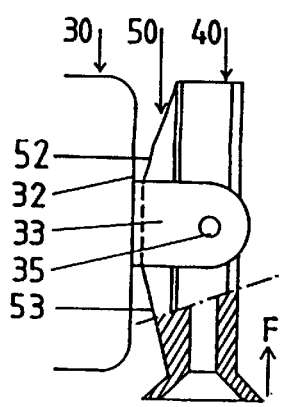
FIGURE 5
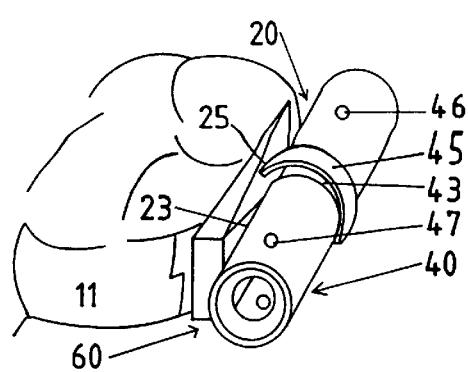

ORTHODONTIC DEVICE

BACKGROUND OF THE INVENTION

The present invention relates to the orthodontic field and concerns a device intending to realign teeth.

A large number of devices intending to move teeth are known, especccially those foryoung children. They concern devices fixed in the mouth, as well as those which have to be worn temporarily during night or day.

It has been established that when a molar has to be displaced distally (in order to create space or to ensure a correct relationship with the lower maxilla) it mostly needs additionally an angular movement in order to bring it in its ideal location.

Devices to ensure translational motion using rigid systems are already described. The shortcomings of these systems are that high friction is exerted between the supporting elements fixed on the tooth and force exerting means system which also impedes any angular movement.

The present invention allows simultaneously angular movement of the tooth toward a predetermined position and translational motion, without any friction and in respect to the individual resistance of the maxillo-dental system of a particular case and without any modification of the orientation of the applied force system. It concerns a device for moving a tooth, comprising a holder fixed to the tooth and a force exerting means able to co-operate at least indirectly with the holder.

Moreover, the devise according to the invention is characterised by the presence of an element which is at least indirectly jointly liable with the applied force system since the element is pivotable in respect to said holder.

Depending on the variation, the pivotable element and/or the holder provides abutments co-operating with each other in the aim to limit the angular movement of the tooth to a predetermined value. Moreover, a cuneal member to adjust the movement of rotation for each particular tooth may be provided.

Depending on the way of execution, the device can be fixed on the tooth directly or by means of a holder fixed around the tooth or can be part of an amovable device.

BRIEF DESCRIPTION OF THE DRAWINGS

The designs attached herewith represent, as a means of a non limited example, different execution forms of the present invention.

FIG. 1 is a sketch of the relative position of the teeth in half an upper jaw and where the upper molar has to be displaced with the use of the device of the present invention which is, in the present design, represented in a schematic way.

The FIGS. 2A and 2B represent the successive phases of displacement of the molar presented in FIG. 1.

FIG. 3 is a perspective view of a first form of execution of the object of the present invention, in a variation where it is fixed on a holder surrounding the tooth.

FIG. 4 is a bird's-eye view of the general effect of FIG. 3, with a partial cut.

FIG. 5 is a perspective view of a second form of execution in a variation where the device according to the present invention, is directly fixed on the tooth.

Figure 6:
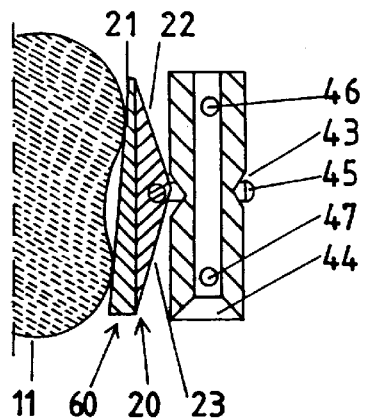

FIG. 6 is a view of a longitudinal cut of the general effect of FIG. 5.

Figure 7:
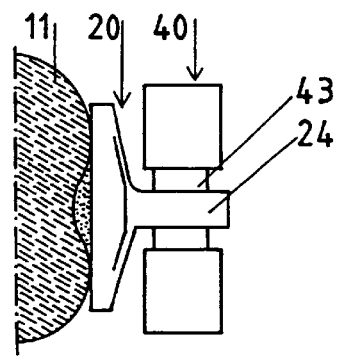

FIG. 7 is a bird's-eye view of the execution in a variation directly fixed on the tooth.

Figure 8:
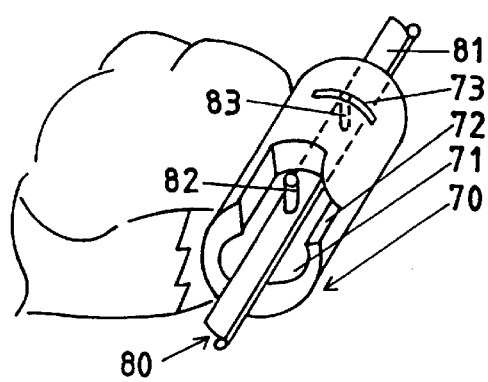

FIG. 8 is a perspective view, with partial pull off, of a fourth form of execution fixed on a holder surrounding the tooth.

Figure 9A:
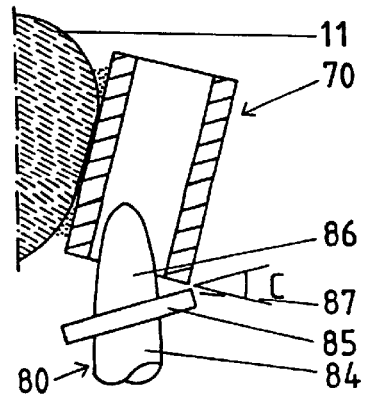
Figure 9B:
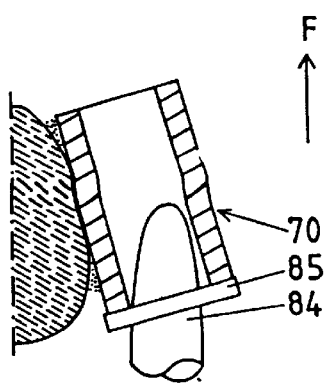

FIGS. 9a and 9b represent cut off views of the extreme positions of a fifth form of execution.

DETAILED DESCRIPTION OF THE PREFERRED EMBODIMENT

According to the schematic implantation of the teeth 10 shown in FIG. 1, one can see that the first bicuspid is represented in contact with bicuspid 12, which has to be displaced. The molar 11 is attached directly with a triangular piece 20 which shows three plane sloping sides 21, 22 and 23.

As one will see subsequently, the displacement of the molar, represented in FIGS. 1 and 2, occur by applying a force in the direction of the arrow F as represented on the design. This displacement is produced either, in an intra-oral way (with the use of means placed between adjacent teeth namely, coils, elastics, magnets, slides, rails, plates), or in an extra-oral way (e.g. with the use of a facial arch which co-operates indirectly with the tooth and presents an outer bow which comes out of the mouth of the patient and is tied behind the neck by elastics). Because such type of appliances are known by the professional, they are not represented in the design.

One will note that the force F on the representation of FIG. 1 is quite parallel on the plane side 22 while plane side 21 of the triangular plane is fixed on the molar 11.

The schematic representations of FIGS. 2A and 2B show respectively the relative positions of the molar 11 which has been angular displaced: firstly the direction of the force F is parallel on the face plane 21, then parallel to the face plane 23. The angular movement of molar 11 is thus represented by the angle, which is the sum between the angle (a) represented in FIG. 1 and the angle (b) represented in FIG. 2B. In respect to the amount of translation of the tooth in the posterior direction according to the arrow F, it is represented in the intermediary phase of FIG. 2A by the separation A and during the phase represented in FIG. 2B by the distance B. Thanks to the present invention, the displacement could be limited to a predeterminate value.

In the previous exposure, we described the present invention where the tooth is fixed to the triangular element 20. The device is destined to be pushed in the direction of the arrow F by a means of displacement which is not represented herewith and which causes the triangular element to pivot. As we will see subsequently, it is possible to obtain an identical relative movement of the tooth itself in relation to the triangular element if this element is fixed to the means of displacement. Moreover, we will note that the clinician is not limited since he can join cuneal member to the triangular element which allows him to limit the rotation to the optimal value of each particular case.

In the variations of FIGS. 3 and 4, we have represented a holder 30 destined to be placed around the tooth which has to be displaced. The edges 30 of the external side 32 of the holder has two wings 33 and 34 which fold up exteriorly to receive a tubular element 40 pivoting on the axis 35. In order to facilitate the insertion of the pushing element in the direction of the arrow F, a wide collarette 41 is provided at the front side of the tubular element 40. In the first execution, the tubular element 40 comprises a lateral prolongation 50 in the direction of the holder.

This prolongation 50 replaces the triangular element previously mentioned and comprises two plane sloping sides 52 and 53. In the initial position, which corresponds with the schema of FIG. 1, plane sloping side 52 leans against the external side 32 of the holder. Due to a pivoting around the axis 35, the tooth can rotate during the movement of translation (for example, by going through the position showed in FIG. 4). At the final position, the plane sloping side 53 of the prolongation 50 will lean against the external side 32 of the holder 30.

In the variations presented in FIGS. 5 and 6, we have represented a second type of execution which is more close to those schematised in FIGS. 1 and 2. Actually, we find again a triangular element 20 which can be either directly attached on the tooth or attached through a cuneal member 60 destined to adapt the molar rotation to each particular case. On the design, we have represented the triangular element 20 and the cuneal member 60 as individual parts. However, it is obvious that both can be realised in one piece.

The triangular element 20 contains an opening 25 attached to the hinge connection with the cylindrical body 40. In the variation represented herewith, the cylindrical body 40 contains a peripheral indentation 43 adapted to the passing over of a fixation ring 45 in the opening 25. To facilitate the introduction of the pushing body in the direction of the arrow, the tubular body 40 presents a conical entrance 44. We have also represented, on the extremities of the tubular body 40, two holes 46 and 47 for connection with the adjacent teeth which are not represented on the drawings. In the initial position which corresponds on the schema of FIG. 1, the side 22 leans against the tubular body 40. Because of pivotable ring 45 in the opening 25, the side 23 will lean against the tubular body when the tooth 11 has been rotated according to the predeterminate value.

In the variation of FIG. 7, the triangular piece is fixed on the tooth either directly or not. In order to ensure its hinging, the triangular piece contains on the top of the triangle a ring 24 which surrounds the peripheral indentation 43 of the tubular body 40. One will note that in the present variation and in those of FIGS. 5 and 6, a supplementary degree of freedom adds to the described swinging compared to FIGS. 3 and 4. "The execution form of FIG. 8 proposes a tubular body 70, which is represented here as fixed to the tooth. The tubular body has an opening 71 which has an elliptical cross-section, intended to fit over of tube 81, which is coupled to the force exerting means 80. The tubular body 70 contains in the present variation, a pair of arcuate slots 72 and 73. The tube 81 has two pins 82 and 83, which ensure the pivoting of the tube 81 inside the opening 71. The pins 82 and 83 protrude through the arcuate slots 72 and 73. The ends of the arcuate slots constitute the stops for the rotation."

The execution forms of the FIGS. 3 to 8 are all represented in the intermediary position corresponding with the schema of FIG. 2A. However, the last variation which will be described in respect to FIGS. 9A and 9B, is represented in the both extreme positions of the angular displacement. In this execution form we will find a tubular body 70 fixed on the tooth directly or by means of a holder which can be fixed or removable. The force exerting means 80 for the displacement in the direction of the arrow F contains here a shaft 84 "equipped with an inclined collar 85. The shaft ends in a rounded end 86."

When the device is inserted and the whole system is in the schematic position of FIG. 1 and represented in FIG. 9A, only the point 87 of the collar contacts on the border of the tubular system 70. After the tooth has been displaced over the angle (c), the entire inclined collarette 85 will lean on the anterior side of the tubular body 70. We see clearly in the representation that if the position in FIG. 9B is obtained, the tooth could only be displaced posteriorly in the direction of the arrow F and will not be able to rotate further. As a variant, we could provide a cylindrical point on this side of the collarette destined to cooperate with a truncated segment.

Numerous other forms of execution could be considered, combining different systems already described and using them in applications based on springs, magnets or others.

I claim:

1. An orthodontic device for moving a tooth translationally and angularly in cooperation with an externally-applied force, comprising:

a holder attached to the tooth;
   a force exerting means for exerting a translational and angular force upon the tooth, coupled to the holder and to the externally-supplied force, comprising:
   a pivotal element coupled to the holder;
   a body element, having a longitudinal axis, coupled to the pivotal element for pivotal movement thereon from a first position through a neutral position to a third position, such that a translational force is exerted upon the tooth when the externally-applied force is applied to the body and an angular force is exerted upon the tooth as the body element pivots from the first position through the neutral position to the third position, while the longitudinal axis of the body element remains aligned with the externally-applied force; and
   stop means for limiting the pivotal movement of the body on the pivotal element to the range from the first position to the third position, such that angular movement of the tooth is limited to a predetermined value.

2. The orthodontic device as in claim 1, in which the pivotal element comprises a triangular element having first, second and third sides, and the stop means comprise the first and second sides of the pivotal element.

3. The orthodontic device as in claim 2, in which the third side of the triangular element is fixed on the tooth and the body element is coupled to the pivotal element opposite the third side, and pivots around a point adjacent the intersection of the first and second sides, such that the first and second side contact the body element, limiting the pivotal movement of the body element.

4. The orthodontic device as in claim 2, in which the third side of the triangular element is fixed on the body element, and the triangular element is coupled to the holder, and the body element and triangular element combination pivots around a point adjacent the intersection of the first and second sides, such that the first and second side contact the holder limiting the pivotal movement of the body element.

5. The orthodontic device of claim 2, in which:

the third side of the triangular element is coupled to the holder;
   the body element comprises a cylindrical element having a peripheral indentation; and
   the pivotal element further comprises a ring element encircling the body element within the peripheral indentation, such that the body element is coupled to the pivotal element opposite the third side, and pivots at the peripheral indentation around a point adjacent the intersection of the first and second sides, such that the first and second side contact the body element, limiting the pivotal movement of the body element.

6. The orthodontic device as in claim 5 in which the holder comprises a separate element fixed on the tooth.

7. The orthodontic device of claim 5, in which the holder is integral with the pivotal element.

8. The orthodontic device as in claim 1 further comprising a cuneal member disposed between the tooth and the holder.

9. The orthodontic device of claim 8, in which the cuneal piece is wedge shaped, such that the cuneal piece may be moved relative to the holder to adjust the angular movement of the tooth.

10. The orthodontic device as in claim 1 in which the holder comprises a separate element fixed on the tooth.

11. The orthodontic device of claim 1, in which the holder is integral with the pivotal element.

12. An orthodontic device for moving a tooth translationally and angularly in cooperation with an externally-applied force, comprising:

a tubular body having a length along a longitudinal axis and inner and outer sides, and an elliptical central opening having a major axis and a minor axis, the tubular body being coupled to the tooth along an outer side such that the major axis of the elliptical central opening is perpendicular to the tooth;

a tube having a longitudinal axis, fitting through the central opening of the tubular body and movably connected thereto, adapted to be coupled to the externally-applied force, such that the externally-applied force is applied along the longitudinal axis of the tube, the tube being capable of pivoting inside the elliptical central opening of the tubular body from a first position through a neutral position to a third position, while the longitudinal axis of the tube remains aligned with the longitudinal axis of the tubular element; and stop means for limiting the pivotal movement of the tube within the elliptical central opening of the tubular body;

such that a translational force is exerted upon the tooth when the externally-applied force is applied to the tube and an angular force is exerted upon the tooth as the tubular body pivots from the first position through the neutral position to the third position.

13. The orthodontic device of claim 12, in which the tubular body has two arched openings extending through from the inner side to the outer side and linearly around the tubular body a preselected length, spaced apart along the longitudinal axis of the tubular body, the tube has a pin extending from the tube through each of the arched openings, and the stop means comprises the interaction of the pins in the slots, such that the angular movement of the tooth is determined by the length of the slots.

14. The orthodontic device of claim 12, further comprising a wedge-shaped cuneal element between the tooth and the tubular body.

15. An orthodontic device for moving a tooth translationally and angularly in cooperation with an externally-applied force, comprising:

a tubular body having an open end, a longitudinal axis and a central opening having a diameter, the tubular body being coupled to the tooth along an outer side;

a tube adapted to be coupled to the externally-applied force, such that the externally-applied force is applied along the longitudinal axis of the tube, the tube having a diameter, a longitudinal axis and a free end, the free end fitting into the central opening of the tubular body through the open end, diameter of the tube being sufficiently less than the diameter of the tubular body such that the tube is capable of pivoting inside the central opening of the tubular body from a first position to a second position;

an inclined collar mounted around the tube, at a preselected angle to the longitudinal axis of the tube, having a diameter greater than the diameter of the central opening of the tubular body, the angle being selected such that when the tube is in the first position the collar contacts only the portion of the open end of the tubular body most distant from the tooth, and when the tube is in the second position the collar contacts substantially all of the open end of the tubular body;

such that a translational force is exerted upon the tooth when the externally-applied force is applied to the tube and an angular force is exerted upon the tooth as the tubular body pivots from the first position to the second position, and the angular movement of the tooth is determined by the angle of the inclined collar to the longitudinal axis of the tube.

16. The orthodontic device of claim 15, further comprising a wedge-shaped cuneal element between the tooth and the tubular body.

17. The orthodontic device of claim 15, in which the free end of the tube is tapered.

* * * * *